United States Patent
Hartley et al.

(10) Patent No.: US 8,703,682 B2
(45) Date of Patent: Apr. 22, 2014

(54) LUBRICATION AND LUBRICATING OIL COMPOSITIONS

(75) Inventors: Joseph P. Hartley, Oxford (GB); Robert G. Rowland, Woodbridge, CT (US); Jie Cheng, Edison, NJ (US); Jacob Emert, Brooklyn, NY (US); Joseph Stieber, Prospect, CT (US)

(73) Assignee: Infineum International Limited (GB)

( * ) Notice: Subject to any disclaimer, the term of this patent is extended or adjusted under 35 U.S.C. 154(b) by 484 days.

(21) Appl. No.: 12/608,039

(22) Filed: Oct. 29, 2009

(65) Prior Publication Data

US 2011/0105372 A1    May 5, 2011

(51) Int. Cl.
*C10M 133/12*    (2006.01)
*C10M 141/10*    (2006.01)
*C07C 211/00*    (2006.01)

(52) U.S. Cl.
USPC .................... 508/557; 508/421; 564/306

(58) Field of Classification Search
USPC .................... 508/557, 421; 564/306
See application file for complete search history.

(56) References Cited

U.S. PATENT DOCUMENTS

| | | | |
|---|---|---|---|
| 5,232,614 A | | 8/1993 | Colclough et al. |
| 6,030,930 A | * | 2/2000 | Emert et al. ............. 508/312 |
| 2007/0006855 A1 | * | 1/2007 | Malandro et al. ........ 123/568.12 |
| 2009/0156441 A1 | * | 6/2009 | Rowland et al. ............. 508/251 |

* cited by examiner

*Primary Examiner* — Vishal Vasisth

(57) ABSTRACT

Tetra-alkylated phenylenediamine compounds useful as ashless TBN sources for lubricating oil compositions that are compatible with fluoroelastomeric engine seal materials and meet copper corrosion requirements, and lubricating oil compositions containing such phenylenediamine compounds.

27 Claims, No Drawings

LUBRICATION AND LUBRICATING OIL COMPOSITIONS

FIELD OF THE INVENTION

This invention relates to phenylenediamine compounds useful as ashless TBN (Total Base Number) boosters for lubricating oil compositions, and lubricating oil compositions, particularly crankcase lubricating oil compositions having reduced levels of sulfated ash (SASH), containing same, and which meet seals compatibility and corrosion test requirements.

BACKGROUND OF THE INVENTION

Environmental concerns have led to continued efforts to reduce the CO, hydrocarbon and nitrogen oxide ($NO_x$) emissions of compression ignited (diesel-fueled) and spark ignited (gasoline-fueled) light duty internal combustion engines. Further, there have been continued efforts to reduce the particulate emissions of compression ignited internal combustion engines. To meet the upcoming emission standards for heavy duty diesel vehicles, original equipment manufacturers (OEMs) may require additional exhaust gas after-treatment devices. Such exhaust gas after-treatment devices may include catalytic converters, which can contain one or more oxidation catalysts, $NO_x$ storage catalysts, and/or $NH_3$ reduction catalysts; and/or a particulate trap.

Oxidation catalysts can become poisoned and rendered less effective by exposure to certain elements/compounds present in engine exhaust gasses, particularly by exposure to phosphorus and phosphorus compounds introduced into the exhaust gas by the degradation of phosphorus-containing lubricating oil additives. Reduction catalysts are sensitive to sulfur and sulfur compounds in the engine exhaust gas introduced by the degradation of both the base oil used to blend the lubricant, and sulfur-containing lubricating oil additives. Particulate traps can become blocked by metallic ash, which is a product of degraded metal-containing lubricating oil additives.

To ensure a long service life, lubricating oil additives that exert a minimum negative impact on such after-treatment devices must be identified, and OEM specifications for "new service fill" and "first fill" heavy duty diesel (HDD) lubricants require maximum sulfur levels of 0.4 mass %; maximum phosphorus levels of 0.12 mass %, and sulfated ash contents below 1.1 mass %, which lubricants are referred to as "mid-SAPS" lubricants (where "SAPS" is an acronym for "Sulfated Ash, Phosphorus, Sulfur"). In the future, OEMs may further restrict these levels maximum levels to 0.08 mass % phosphorus, 0.2 mass % sulfur and 0.8 mass % sulfated ash, with such lubricants being referred to as "low-SAPS" lubricating oil compositions.

As the amounts of phosphorus, sulfur and ash-containing lubricant additives are being reduced to provide mid- and low-SAPS lubricants that are compatible with exhaust gas after-treatment devices, the lubricating oil composition must continue to provide the high levels of lubricant performance, including adequate detergency, dictated by the "new service", and "first fill" specifications of the OEM's, such as the ACEA E6 and MB p228.51 (European) and API CI-4+ and API CJ-4 (U.S.) specifications for heavy duty engine lubricants. Criteria for being classified as a lubricating oil composition meeting the above listed industry standards are known to those skilled in the art.

The ability of a lubricant to neutralize acidic byproducts of combustion, the amounts of which increase in engines provided with exhaust gas recirculation (EGR) systems, particularly condensed EGR systems in which exhaust gasses are cooled prior to recirculation, can be improved, and the drain interval of the lubricant can be extended, by increasing the total base number (TBN) of the composition. Hitherto, TBN has been provided by overbased detergents that introduce sulfated ash into the composition. It would be advantageous to provide a lubricating oil composition with a high level of TBN using a TBN boosting component that does not contribute sulfated ash. As highly basic components are known to induce corrosion and, in some cases reduce the compatibility between lubricating oil compositions and the fluoroelastomeric seal materials used in engines, it would be preferable to provide such a component that does not induce corrosion and, does not adversely affect seals compatibility. Due to demands for improved fuel economy, less viscous lubricants, such as 0 W and 5 W 20 and 30 grade lubricants, have become more prevalent. To allow for easier formulation of such lubricants, the amount of polymer introduced by additives is preferably minimized. Therefore, it would be further preferable to provide a non-polymeric ashless TBN source.

U.S. Pat. Nos. 5,525,247; 5,672,570; and 6,569,818 are directed to "low ash" lubricating oil compositions in which sulfated ash content is reduced by replacing overbased detergents with neutral detergents. These patents describe such lubricants as providing sufficient detergency, but do not describe that they provide sufficient TBN for use, for example, in HDD engines. US Patent Application 2007/0203031 describes the use of high TBN nitrogen-containing dispersants as ashless TBN sources.

U.S. Pat. No. 5,232,614 describes substituted para-phenylenediamine compounds as effective anti-oxidants for lubricating oil compositions.

SUMMARY OF THE INVENTION

The present invention addresses the above-mentioned problems by providing certain tetra-alkylated phenylenediamine compounds as ashless TBN boosters in lubricating oil compositions that meet seals compatibility and corrosion test requirements.

In accordance with a first aspect of the invention, there is provided a N,N'-tetra-aliphatic hydrocarbylated phenylenediamine wherein one to three of the hydrocarbyl (e.g. alkyl) groups are branched at an alpha carbon atom and have 3 to 12 carbon atoms and one to three of the hydrocarbyl (e.g. alkyl) groups are branched at a beta carbon atom, and have 4 to 12 carbon atoms.

In accordance with a second aspect of the invention, there is provided a crankcase lubricating oil composition such as a heavy duty diesel lubricating oil comprising or made by admixing an oil of lubricating viscosity, in a major amount, and, one or more phenylenediamine compounds of the first aspect, in minor amounts.

In accordance with a third aspect of the present invention, there is provided a method of increasing the TBN, according to ASTM D4739, of a lubricating oil composition without concurrently increasing the SASH content of the composition, which method comprises incorporating into the composition, in a minor amount, one or more phenylenediamine compounds, as defined in the first aspect of the invention, such that the composition has copper corrosion performance in the high-temperature bench corrosion test (ASTM D6594) that falls within the limits of the API CJ-4 and ACEA E6 specification, and has fluoroelastomeric engine seal materials compatibility performance in the MB-AK6 test that falls within the limits of the MB p228.51 specification.

In accordance with a fourth aspect of the invention, there is provided a method of lubricating surfaces of a compression-ignited internal combustion engine during its operation comprising:

(a) providing, in a minor amount, one or more phenylenediamine compounds, as defined in the first aspect of the invention, in a major amount of an oil of lubricating viscosity to make a lubricating oil composition, the TBN of which, as measured by ASTM D4739, is thereby enhanced without concurrently increasing the SASH, and that the composition has copper corrosion performance in the high-temperature bench corrosion test (ASTM D6594) that falls within the limits of the API CJ-4 and ACEA E6 specification, and has fluoroelastomeric engine seal materials compatibility performance in the MB-AK6 test that falls within the limits of the MB p228.51 specification;

(b) providing the lubricating oil composition to the engine crankcase; and (c) operating the engine.

In accordance with a fifth aspect of the invention, there are provided lubricating oil compositions, as in the second aspect, meeting the performance criteria of one or more of the ACEA E6, MB p228.51, API CI-4+ and API CJ-4 specifications for heavy duty engine lubricants.

In accordance with a sixth aspect of the invention, there is provided a heavy duty diesel engine equipped with an exhaust gas recirculation (EGR) system, preferably a condensed EGR system and a particulate trap, the crankcase of which engine is lubricated with a lubricating oil composition of the second aspect.

In accordance with a seventh aspect of the invention, there is provided a method for forming a high TBN lubricant having a reduced SASH content comprising incorporating into said lubricating oil composition one or more phenylenediamine compounds of the first aspect.

In this specification, the following words and expressions, if and when used, have the meanings ascribed below:

"active ingredient" or "(a.i.)" refers to additive material that is not diluent or solvent;

"comprising" or any cognate word specifies the presence of stated features, steps, or integers or components, but does not preclude the presence or addition of one or more other features, steps, integers, components or groups thereof; the expressions "consists of" or "consists essentially of" or cognates may be embraced within "comprises" or cognates, wherein "consists essentially of" permits inclusion of substances not materially affecting the characteristics of the composition to which it applies;

"major amount" means in excess of 50 mass % of a composition;

"minor amount" means less than 50 mass % of a composition;

"TBN" means total base number as measured by ASTM D2896 or ASTM D4739, as indicated.

Furthermore in this specification:

"phosphorus content" is as measured by ASTM D5185;

"sulphated ash content" is as measured by ASTM D874;

"sulphur content" is as measured by ASTM D2622;

"KV100" means kinematic viscosity at 100° C. as measured by ASTM D445; and

"Hydrocarbyl", and cognate words, refer to groups that contain carbon and hydrogen atoms and that are bonded to the remainder of the molecule directly via a carbon atom. They may contain hetero atoms provided such hetero atoms do not affect the essentially hydrocarbon nature of the hydrocarbyl groups.

Also, it will be understood that various components used, essential as well as optimal and customary, may react under conditions of formulation, storage or use and that the invention also provides the product obtainable or obtained as a result of any such reaction.

Further, it is understood that any upper and lower quality, range and ratio limits set forth herein may be independently combined.

DETAILED DESCRIPTION OF THE INVENTION

N,N'-tetra-aliphatic hydrocarbyl phenylenediamine compounds of the invention are found to contribute to the TBN of a lubricant as measured in ASTM D2896 and also as measured in ASTM D4739. Further, as demonstrated in the examples of this specification, the specified phenylenediamine compounds do not cause lubricants to fail any of the seals compatibility tests such in the MBSEAL-2/AK6 test, and do not cause lubricants to fail any of the HTCBT tests as described in ASTM D6594, in particular the copper corrosion test thereof.

N-N'-tetra-aliphatic hydrocarbyl phenylenediamine compounds useful in this invention may be depicted by the formula below:

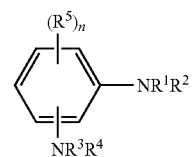

(I)

wherein each of $R^1$, $R^2$, $R^3$ and $R^4$ is independently an aliphatic hydrocarbyl group, preferably an alkyl group, having 3 to 12 carbon atoms, at least one of $R^1$, $R^2$, $R^3$ and $R^4$ being an alkyl group branched in the position alpha to the attached nitrogen and having 3 to 12 carbon atoms, and at least one of $R^1$, $R^2$, $R^3$ and $R^4$ being an alkyl group branched in the position beta to the attached nitrogen, having 4 to 12 carbon atoms;

$R^5$, or each $R^5$, is independently hydrogen or an aliphatic hydrocarbyl group, preferably an alkyl group, having 1 to 12 carbon atoms; and n is from 0 to 4.

Preferred are phenylenediamines of the above formula wherein each of $R^1$ and $R^3$ is independently an alkyl group branched in the position alpha to the attached nitrogen atom, having 3 to 12 carbon atoms; and each of $R^2$ and $R^4$ is independently an alkyl group branched in the position beta to the attached nitrogen atom, having 4 to 12 carbon atoms.

Preferably, the phenylenediamine compounds useful in this invention have a TBN (measured as in ASTM D-2896 and/or ASTM D4739, preferably measured as in ASTM D4739) of at least 50, such as at least 100, preferably at least 120 mg KOH/g.

Phenylenediamines of the present invention may be in the form of a single compound, or may be a mixture of compounds of the above formula.

Preferably, the phenylenediamine of the present invention has, or have on average, a molecular weight of from 450 to 700, such as from 450 to 650, preferably from 500 to 600

Preferably, the nitrogen atoms are arranged para to one another.

The phenylenediamine compounds useful in the invention may be made by methods such as those known in the art.

Lubricating oil compositions of the present invention comprise a major amount of an oil of lubricating viscosity and a minor amount of one or more of the specified phenylenediamine compounds.

Oils of lubricating viscosity useful in the context of the present invention may be selected from natural lubricating oils, synthetic lubricating oils and mixtures thereof. The lubricating oil may range in viscosity from light distillate mineral oils to heavy lubricating oils such as gasoline engine oils, mineral lubricating oils and heavy duty diesel oils. Generally, the viscosity of the oil ranges from 2 to 40, especially from 4 to 20, $mm^2s^{-1}$ as measured at 100° C.

Natural oils include animal oils and vegetable oils (e.g., castor oil, lard oil); liquid petroleum oils and hydrorefined, solvent-treated or acid-treated mineral oils of the paraffinic, naphthenic and mixed paraffinic-naphthenic types. Oils of lubricating viscosity derived from coal or shale also serve as useful base oils.

Synthetic lubricating oils include hydrocarbon oils and halo-substituted hydrocarbon oils such as polymerized and interpolymerized olefins (e.g., polybutylenes, polypropylenes, propylene-isobutylene copolymers, chlorinated polybutylenes, poly(1-hexenes), poly(1-octenes), poly(1-decenes)); alkylbenzenes (e.g., dodecylbenzenes, tetradecylbenzenes, dinonylbenzenes, di(2-ethylhexyl)benzenes); polyphenyls (e.g., biphenyls, terphenyls, alkylated polyphenols); and alkylated diphenyl ethers and alkylated diphenyl sulfides and derivative, analogs and homologs thereof. Also useful are synthetic oils derived from a gas to liquid process from Fischer-Tropsch synthesized hydrocarbons, which are commonly referred to as gas to liquid, or "GTL" base oils.

Alkylene oxide polymers and interpolymers and derivatives thereof where the terminal hydroxyl groups have been modified by esterification, etherification, etc., constitute another class of known synthetic lubricating oils. These are exemplified by polyoxyalkylene polymers prepared by polymerization of ethylene oxide or propylene oxide, and the alkyl and aryl ethers of polyoxyalkylene polymers (e.g., methyl-polyiso-propylene glycol ether having a molecular weight of 1000 or diphenyl ether of poly-ethylene glycol having a molecular weight of 1000 to 1500); and mono- and polycarboxylic esters thereof, for example, the acetic acid esters, mixed $C_3$-$C_8$ fatty acid esters and $C_{13}$ oxo acid diester of tetraethylene glycol.

Another suitable class of synthetic lubricating oils comprises the esters of dicarboxylic acids (e.g., phthalic acid, succinic acid, alkyl succinic acids and alkenyl succinic acids, maleic acid, azelaic acid, suberic acid, sebacic acid, fumaric acid, adipic acid, linoleic acid dimer, malonic acid, alkylmalonic acids, alkenyl malonic acids) with a variety of alcohols (e.g., butyl alcohol, hexyl alcohol, dodecyl alcohol, 2-ethylhexyl alcohol, ethylene glycol, diethylene glycol monoether, propylene glycol). Specific examples of such esters includes dibutyl adipate, di(2-ethylhexyl)sebacate, di-n-hexyl fumarate, dioctyl sebacate, diisooctyl azelate, diisodecyl azelate, dioctyl phthalate, didecyl phthalate, dieicosyl sebacate, the 2-ethylhexyl diester of linoleic acid dimer, and the complex ester formed by reacting one mole of sebacic acid with two moles of tetraethylene glycol and two moles of 2-ethylhexanoic acid.

Esters useful as synthetic oils also include those made from $C_5$ to $C_{12}$ monocarboxylic acids and polyols and polyol esters such as neopentyl glycol, trimethylolpropane, pentaerythritol, dipentaerythritol and tripentaerythritol.

Silicon-based oils such as the polyalkyl-, polyaryl-, polyalkoxy- or polyaryloxysilicone oils and silicate oils comprise another useful class of synthetic lubricants; such oils include tetraethyl silicate, tetraisopropyl silicate, tetra-(2-ethylhexyl) silicate, tetra-(4-methyl-2-ethylhexyl)silicate, tetra-(p-tert-butyl-phenyl)silicate, hexa-(4-methyl-2-ethylhexyl)disiloxane, poly(methyl)siloxanes and poly(methylphenyl) siloxanes. Other synthetic lubricating oils include liquid esters of phosphorous-containing acids (e.g., tricresyl phosphate, trioctyl phosphate, diethyl ester of decylphosphonic acid) and polymeric tetrahydrofurans.

The oil of lubricating viscosity may comprise a Group I, Group II or Group III, base stock or base oil blends of the aforementioned base stocks. Preferably, the oil of lubricating viscosity is a Group II or Group III base stock, or a mixture thereof, or a mixture of a Group I base stock and one or more a Group II and Group III. Preferably, a major amount of the oil of lubricating viscosity is a Group II, Group III, Group IV or Group V base stock, or a mixture thereof. The base stock, or base stock blend preferably has a saturate content of at least 65, more preferably at least 75, such as at least 85, %. Most preferably, the base stock, or base stock blend, has a saturate content of greater than 90%. Preferably, the oil or oil blend has a sulfur content of less than 1, preferably less than 0.6, most preferably less than 0.4, % by weight.

Preferably the volatility of the oil or oil blend, as measured by the Noack volatility test (ASTM D5880), is less than or equal to 30, preferably less than or equal to 25, more preferably less than or equal to 20, most preferably less than or equal to 16, %. Preferably, the viscosity index (VI) of the oil or oil blend is at least 85, preferably at least 100, most preferably from about 105 to 140.

Definitions for the base stocks and base oils in this invention are the same as those found in the American Petroleum Institute (API) publication "Engine Oil Licensing and Certification System", Industry Services Department, Fourteenth Edition, December 1996, Addendum 1, December 1998. Said publication categorizes base stocks as follows:

a) Group I base stocks contain less than 90 percent saturates and/or greater than 0.03 percent sulfur and have a viscosity index greater than or equal to 80 and less than 120 using the test methods specified in Table 1.
b) Group II base stocks contain greater than or equal to 90 percent saturates and less than or equal to 0.03 percent sulfur and have a viscosity index greater than or equal to 80 and less than 120 using the test methods specified in Table 1.
c) Group III base stocks contain greater than or equal to 90 percent saturates and less than or equal to 0.03 percent sulfur and have a viscosity index greater than or equal to 120 using the test methods specified in Table 1.
d) Group IV base stocks are polyalphaolefins (PAO).
e) Group V base stocks include all other base stocks not included in Group I, II, III, or IV.

TABLE I

Analytical Methods for Base Stock

| Property | Test Method |
|---|---|
| Saturates | ASTM D 2007 |
| Viscosity Index | ASTM D 2270 |
| Sulfur | ASTM D 2622 |
|  | ASTM D 4294 |
|  | ASTM D 4927 |
|  | ASTM D 3120 |

Metal-containing or ash-forming detergents function both as detergents to reduce or remove deposits and as acid neutralizers or rust inhibitors, thereby reducing wear and corrosion and extending engine life. Detergents generally comprise a polar head with a long hydrophobic tail, with the polar head comprising a metal salt of an acidic organic compound. The salts may contain a substantially stoichiometric amount of the metal in which case they are usually described as normal or neutral salts, and would typically have a total base number or TBN (as can be measured by ASTM D2896) of from 0 to 80. A large amount of a metal base may be incorporated by reacting excess metal compound (e.g., an oxide or hydroxide) with an acidic gas (e.g., carbon dioxide). The resulting overbased detergent comprises neutralized detergent as the outer layer of a metal base (e.g. carbonate) micelle. Such overbased detergents may have a TBN of 150 or greater, and typically will have a TBN of from 250 to 450 or more. In the presence of the hydrocarbylated phenylenediamine compound of the present invention, the amount of overbased detergent can be reduced, or detergents having reduced levels of overbasing (e.g., detergents having a TBN of 100 to 200), or neutral detergents can be employed, resulting in a corresponding reduction in the SASH content of the lubricating oil composition without a reduction in the acid neutralizing performance thereof.

Detergents that may be used include oil-soluble neutral and overbased sulfonates, phenates, sulfurized phenates, thiophosphonates, salicylates, and naphthenates and other oil-soluble carboxylates of a metal, particularly the alkali or alkaline earth metals, e.g., sodium, potassium, lithium, calcium, and magnesium. The most commonly used metals are calcium and magnesium, which may both be present in detergents used in a lubricant, and mixtures of calcium and/or magnesium with sodium. Particularly convenient metal detergents are neutral and overbased calcium sulfonates having TBN of from 20 to 450 TBN, and neutral and overbased calcium phenates and sulfurized phenates having TBN of from 50 to 450. Combinations of detergents, whether overbased or neutral or both, may be used.

Sulfonates may be prepared from sulfonic acids which are typically obtained by the sulfonation of alkyl substituted aromatic hydrocarbons such as those obtained from the fractionation of petroleum or by the alkylation of aromatic hydrocarbons. Examples included those obtained by alkylating benzene, toluene, xylene, naphthalene, diphenyl or their halogen derivatives such as chlorobenzene, chlorotoluene and chloronaphthalene. The alkylation may be carried out in the presence of a catalyst with alkylating agents having from about 3 to more than 70 carbon atoms. The alkaryl sulfonates usually contain from about 9 to about 80 or more carbon atoms, preferably from about 16 to about 60 carbon atoms per alkyl substituted aromatic moiety.

The oil-soluble sulfonates or alkaryl sulfonic acids may be neutralized with oxides, hydroxides, alkoxides, carbonates, carboxylate, sulfides, hydrosulfides, nitrates, borates and ethers of the metal. The amount of metal compound is chosen having regard to the desired TBN of the final product but typically ranges from about 100 to 220 mass % (preferably at least 125 mass %) of that stoichiometrically required.

Metal salts of phenols and sulfurized phenols are prepared by reaction with an appropriate metal compound such as an oxide or hydroxide and neutral or overbased products may be obtained by methods well known in the art. Sulfurized phenols may be prepared by reacting a phenol with sulfur or a sulfur containing compound such as hydrogen sulfide, sulfur monohalide or sulfur dihalide, to form products which are generally mixtures of compounds in which two or more phenols are bridged by sulfur-containing bridges.

Lubricating oil compositions of the present invention may further contain one or more ashless dispersants, which effectively reduce formation of deposits upon use in gasoline and diesel engines, when added to lubricating oils. Ashless dispersants useful in the compositions of the present invention comprises an oil soluble polymeric long chain backbone having functional groups capable of associating with particles to be dispersed. Typically, such dispersants comprise amine, alcohol, amide or ester polar moieties attached to the polymer backbone, often via a bridging group. The ashless dispersant may be, for example, selected from oil-soluble salts, esters, amino-esters, amides, imides and oxazolines of long chain hydrocarbon-substituted mono- and polycarboxylic acids or anhydrides thereof; thiocarboxylate derivatives of long chain hydrocarbons; long chain aliphatic hydrocarbons having polyamine moieties attached directly thereto; and Mannich condensation products formed by condensing a long chain substituted phenol with formaldehyde and polyalkylene polyamine. The most common dispersant in use is the well-known succinimide dispersant, which is a condensation product of a hydrocarbyl-substituted succinic anhydride and a poly(alkyleneamine). Both mono-succinimide and bis-succinimide dispersants (and mixtures thereof) are well known.

Preferably, the ashless dispersant is a "high molecular weight" dispersant having a number average molecular weight ($\overline{M}_n$) greater than or equal to 4,000, such as between 4,000 and 20,000. The precise molecular weight ranges will depend on the type of polymer used to form the dispersant, the number of functional groups present, and the type of polar functional group employed. For example, for a polyisobutylene derivatized dispersant, a high molecular weight dispersant is one formed with a polymer backbone having a number average molecular weight of from 1680 to 5600. Typical commercially available polyisobutylene-based dispersants contain polyisobutylene polymers having a number average molecular weight ranging from about 900 to 2300, functionalized by maleic anhydride (MW=98), and derivatized with polyamines having a molecular weight of from 100 to 350. Polymers of lower molecular weight may also be used to form high molecular weight dispersants by incorporating multiple polymer chains into the dispersant, which can be accomplished using methods that are know in the art.

Preferred groups of dispersant include polyamine-derivatized poly α-olefin, dispersants, particularly ethylene/butene alpha-olefin and polyisobutylene-based dispersants. Particularly preferred are ashless dispersants derived from polyisobutylene substituted with succinic anhydride groups and reacted with polyethylene amines, e.g., polyethylene diamine, tetraethylene pentamine; or a polyoxyalkylene polyamine, e.g., polyoxypropylene diamine, trimethylolaminomethane; a hydroxy compound, e.g., pentaerythritol; and combinations thereof. One particularly preferred dispersant combination is a combination of (A) polyisobutylene substituted with succinic anhydride groups and reacted with (B) a hydroxy compound, e.g., pentaerythritol; (C) a polyoxyalkylene polyamine, e.g., polyoxypropylene diamine, or (D) a polyalkylene diamine, e.g., polyethylene diamine and tetraethylene pentamine using about 0.3 to about 2 moles of (B), (C) and/or (D) per mole of (A). Another preferred dispersant combination comprises a combination of (A) polyisobutenyl succinic anhydride with (B) a polyalkylene polyamine, e.g., tetraethylene pentamine, and (C) a polyhydric alcohol or polyhydroxy-substituted aliphatic primary amine, e.g., pentaerythritol or trimethylolaminomethane, as described in U.S. Pat. No. 3,632,511.

Another class of ashless dispersants comprises Mannich base condensation products. Generally, these products are prepared by condensing about mole of an alkyl-substituted mono- or polyhydroxy benzene with 1 to 2.5 moles of carbonyl compound(s) (e.g., formaldehyde and paraformaldehyde) and 0.5 to 2 moles of polyalkylene polyamine, as disclosed, for example, in U.S. Pat. No. 3,442,808. Such Mannich base condensation products may include a polymer product of a metallocene catalyzed polymerization as a substituent on the benzene group, or may be reacted with a compound containing such a polymer substituted on a succinic anhydride in a manner similar to that described in U.S. Pat. No. 3,442,808. Examples of functionalized and/or derivatized olefin polymers synthesized using metallocene catalyst systems are described in the publications identified supra.

The dispersant can be further post treated by a variety of conventional post treatments such as boration, as generally taught in U.S. Pat. Nos. 3,087,936 and 3,254,025. Boration of the dispersant is readily accomplished by treating an acyl nitrogen-containing dispersant with a boron compound such as boron oxide, boron halide boron acids, and esters of boron acids, in an amount sufficient to provide from 0.1 to 20 atomic proportions of boron for each mole of acylated nitrogen composition. Useful dispersants contain from 0.05 to 2.0, e.g., from 0.05 to 0.7, mass % boron. The boron, which appears in the product as dehydrated boric acid polymers (primarily $(HBO_2)_3$), is believed to attach to the dispersant imides and diimides as amine salts, e.g., the metaborate salt of the diimide. Boration can be carried out by adding from 0.5 to 4, e.g., from 1 to 3, mass % (based on the mass of acyl nitrogen compound) of a boron compound, preferably boric acid, usually as a slurry, to the acyl nitrogen compound and heating with stirring at from 135 to 190, e.g., 140 to 170, ° C., for from 1 to 5 hours, followed by nitrogen stripping. Alternatively, the boron treatment can be conducted by adding boric acid to a hot reaction mixture of the dicarboxylic acid material and amine, while removing water. Other post-reaction processes commonly known in the art can also be applied.

The dispersant may also be further post treated by reaction with a so-called "capping agent". Conventionally, nitrogen-containing dispersants have been "capped" to reduce the adverse effect such dispersants have on the fluoroelastomer engine seals. Numerous capping agents and methods are known. Of the known "capping agents", those that convert basic dispersant amino groups to non-basic moieties (e.g., amido or imido groups) are most suitable. The reaction of a nitrogen-containing dispersant and alkyl acetoacetate (e.g., ethyl acetoacetate (EAA)) is described, for example, in U.S. Pat. Nos. 4,839,071; 4,839,072 and 4,579,675. The reaction of a nitrogen-containing dispersant and formic acid is described, for example, in U.S. Pat. No. 3,185,704. The reaction product of a nitrogen-containing dispersant and other suitable capping agents are described in U.S. Pat. No. 4,663,064 (glycolic acid); U.S. Pat. Nos. 4,612,132; 5,334,321; 5,356,552; 5,716,912; 5,849,676; 5,861,363 (alkyl and alkylene carbonates, e.g., ethylene carbonate); U.S. Pat. No. 5,328,622 (mono-epoxide); U.S. Pat. Nos. 5,026,495; 5,085,788; 5,259,906; 5,407,591 (poly (e.g., bis)-epoxides) and U.S. Pat. No. 4,686,054 (maleic anhydride or succinic anhydride). The foregoing list is not exhaustive and other methods of capping nitrogen-containing dispersants are known to those skilled in the art.

For adequate piston deposit control, a nitrogen-containing dispersant can be added in an amount providing the lubricating oil composition with from 0.03 to 0.15, preferably from 0.07 to 0.12, mass % of nitrogen.

Ashless dispersants are basic in nature and therefore have a TBN which, depending on the nature of the polar group and whether or not the dispersant is borated or treated with a capping agent, may be from 5 to 200 mg KOH/g. However, high levels of basic dispersant nitrogen are known to have a deleterious effect on the fluoroelastomeric materials conventionally used to form engine seals and, therefore, it is preferable to use the minimum amount of dispersant necessary to provide piston deposit control, and to use substantially no dispersant, or preferably no dispersant, having a TBN of greater than 5 mg KOH/g. Preferably, the amount of dispersant employed will contribute no more than 4, preferably no more than 3 mg KOH/g of TBN to the lubricating oil composition. It is further preferable that dispersant provides no greater than 30, preferably no greater than 25, more preferably less than 20% of the total TBN of the lubricating oil composition.

Additional additives may be incorporated in the compositions of the invention to enable them to meet particular requirements. Examples of additives which may be included in the lubricating oil compositions are metal rust inhibitors, viscosity index improvers, corrosion inhibitors, oxidation inhibitors, friction modifiers, other dispersants, anti-foaming agents, anti-wear agents and pour point depressants. Some are discussed in further detail below.

Dihydrocarbyl dithiophosphate metal salts are frequently used as antiwear and antioxidant agents. The metal may be an alkali or alkaline earth metal, or aluminum, lead, tin, molybdenum, manganese, nickel, copper or zinc, zinc being preferred. The zinc salts are most commonly used in lubricating oil in amounts of 0.1 to 10, preferably 0.2 to 2, wt. %, based upon the total weight of the lubricating oil composition. They may be prepared in accordance with known techniques by first forming a dihydrocarbyl dithiophosphoric acid (DDPA), usually by reaction of one or more alcohol or a phenol with $P_2S_5$ and then neutralizing the formed DDPA with a zinc compound. For example, a dithiophosphoric acid may be made by reacting mixtures of primary and secondary alcohols. Alternatively, multiple dithiophosphoric acids can be prepared where the hydrocarbyl groups on one are entirely secondary in character and the hydrocarbyl groups on the others are entirely primary in character. To make the zinc salt, any basic or neutral zinc compound could be used but the oxides, hydroxides and carbonates are most generally employed. Commercial additives frequently contain an excess of zinc due to the use of an excess of the basic zinc compound in the neutralization reaction.

The preferred zinc dihydrocarbyl dithiophosphates are oil-soluble salts of dihydrocarbyl dithiophosphoric acids and may be represented by the following formula:

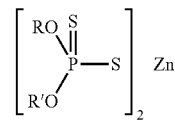

wherein R and R' may be the same or different hydrocarbyl radicals containing from 1 to 18, preferably 2 to 12, carbon atoms and including radicals such as alkyl, alkenyl, aryl, arylalkyl, alkaryl and cycloaliphatic radicals. Particularly preferred as R and R' groups are alkyl groups of 2 to 8 carbon atoms. Thus, the radicals may, for example, be ethyl, n-propyl, i-propyl, n-butyl, i-butyl, sec-butyl, amyl, n-hexyl, i-hexyl, n-octyl, decyl, dodecyl, octadecyl, 2-ethylhexyl, phenyl, butylphenyl, cyclohexyl, methylcyclopentyl, propenyl, butenyl. In order to obtain oil solubility, the total number of carbon atoms (i.e. R and R') in the dithiophosphoric acid will generally be about 5 or greater. The zinc dihydrocarbyl dithiophosphate can therefore comprise zinc dialkyl dithiophosphates. The present invention may be particularly useful when used with lubricant compositions containing phosphorus levels of from about 0.02 to about 0.12 mass %, such as from about 0.03 to about 0.10 mass %, or from about 0.05 to about 0.08 mass %, based on the total mass of the composition. In one preferred embodiment, lubricating oil compositions of the present invention contain zinc dialkyl dithiophosphate derived predominantly (e.g., over 50 mol. %, such as over 60 mol. %) from secondary alcohols.

Oxidation inhibitors or antioxidants reduce the tendency of mineral oils to deteriorate in service. Oxidative deterioration can be evidenced by sludge in the lubricant, varnish-like deposits on the metal surfaces, and by viscosity growth. Such oxidation inhibitors include hindered phenols, alkaline earth metal salts of alkylphenolthioesters having preferably $C_5$ to $C_{12}$ alkyl side chains, calcium nonylphenol sulfide, oil soluble phenates and sulfurized phenates, phosphosulfurized or sulfurized hydrocarbons, phosphorous esters, metal thiocarbamates, oil soluble copper compounds as described in U.S. Pat. No. 4,867,890, and molybdenum-containing compounds.

Typical oil-soluble aromatic amines having at least two aromatic groups attached directly to one amine nitrogen contain from 6 to 16 carbon atoms. The amines may contain more than two aromatic groups. Compounds having a total of at least three aromatic groups in which two aromatic groups are linked by a covalent bond or by an atom or group (e.g., an oxygen or sulfur atom, or a —CO—, —SO$_2$— or alkylene group) and two are directly attached to one amine nitrogen also considered aromatic amines having at least two aromatic groups attached directly to the nitrogen. The aromatic rings are typically substituted by one or more substituents selected from alkyl, cycloalkyl, alkoxy, aryloxy, acyl, acylamino, hydroxy, and nitro groups.

Multiple antioxidants are commonly employed in combination. In one preferred embodiment, lubricating oil compositions of the present invention contain from 0.1 to 1.2 mass % of aminic antioxidant and from 0.1 to 3 mass % of phenolic antioxidant. In another preferred embodiment, lubricating oil compositions of the present invention contain from 0.1 to 1.2 mass % of aminic antioxidant, from 0.1 to 3 mass % of phenolic antioxidant and a molybdenum compound in an amount providing the lubricating oil composition from 10 to 1000 ppm of molybdenum.

Representative examples of suitable viscosity modifiers are polyisobutylene, copolymers of ethylene and propylene, polymethacrylates, methacrylate copolymers, copolymers of an unsaturated dicarboxylic acid and a vinyl compound, interpolymers of styrene and acrylic esters, and partially hydrogenated copolymers of styrene/isoprene, styrene/butadiene, and isoprene/butadiene, as well as the partially hydrogenated homopolymers of butadiene and isoprene.

Friction modifiers and fuel economy agents that are compatible with the other ingredients of the final oil may also be included. Examples of such materials include glyceryl monoesters of higher fatty acids, for example, glyceryl monooleate; esters of long chain polycarboxylic acids with diols, for example, the butane diol ester of a dimerized unsaturated fatty acid; oxazoline compounds; and alkoxylated alkyl-substituted mono-amines, diamines and alkyl ether amines, for example, ethoxylated tallow amine and ethoxylated tallow ether amine.

Other known friction modifiers comprise oil-soluble organo-molybdenum compounds. Such organo-molybdenum friction modifiers also provide antioxidant and antiwear credits to a lubricating oil composition. Examples of such oil soluble organo-molybdenum compounds include dithiocarbamates, dithiophosphates, dithiophosphinates, xanthates, thioxanthates, sulfides, and the like, and mixtures thereof. Particularly preferred are molybdenum dithiocarbamates, dialkyldithiophosphates, alkyl xanthates and alkylthioxanthates.

Additionally, the molybdenum compound may be an acidic molybdenum compound. These compounds will react with a basic nitrogen compound as measured by ASTM test D-664 or D-2896 titration procedure and are typically hexavalent. Included are molybdic acid, ammonium molybdate, sodium molybdate, potassium molybdate, and other alkaline metal molybdates and other molybdenum salts, e.g., hydrogen sodium molybdate, $MoOCl_4$, $MoO_2Br_2$, $Mo_2O_3Cl_6$, molybdenum trioxide or similar acidic molybdenum compounds.

Among the molybdenum compounds useful in the compositions of this invention are organo-molybdenum compounds of the formulae:

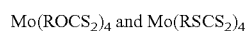

$$Mo(ROCS_2)_4 \text{ and } Mo(RSCS_2)_4$$

wherein R is an organo group selected from the group consisting of alkyl, aryl, aralkyl and alkoxyalkyl, generally of from 1 to 30 carbon atoms, and preferably 2 to 12 carbon atoms and most preferably alkyl of 2 to 12 carbon atoms. Especially preferred are the dialkyldithiocarbamates of molybdenum.

Another group of organo-molybdenum compounds useful in the lubricating compositions of this invention are trinuclear molybdenum compounds, especially those of the formula $Mo_3S_kL_nQ_z$ and mixtures thereof wherein the L are independently selected ligands having organo groups with a sufficient number of carbon atoms to render the compound soluble or dispersible in the oil, n is from 1 to 4, k varies from 4 through 7, Q is selected from the group of neutral electron donating compounds such as water, amines, alcohols, phosphines, and ethers, and z ranges from 0 to 5 and includes non-stoichiometric values. At least 21 total carbon atoms should be present among all the ligand organo groups, such as at least 25, at least 30, or at least 35 carbon atoms.

A dispersant-viscosity index improver functions as both a viscosity index improver and as a dispersant. Examples of dispersant-viscosity index improvers include reaction products of amines, for example polyamines, with a hydrocarbyl-substituted mono- or di-carboxylic acid in which the hydrocarbyl substituent comprises a chain of sufficient length to impart viscosity index improving properties to the compounds. In general, the viscosity index improver dispersant may be, for example, a polymer of a $C_4$ to $C_{24}$ unsaturated ester of vinyl alcohol or a $C_3$ to $C_{10}$ unsaturated mono-carboxylic acid or a $C_4$ to $C_{10}$ di-carboxylic acid with an unsaturated nitrogen-containing monomer having 4 to 20 carbon atoms; a polymer of a $C_2$ to $C_{20}$ olefin with an unsaturated $C_3$ to $C_{10}$ mono- or di-carboxylic acid neutralized with an amine, hydroxyl amine or an alcohol; or a polymer of ethylene with a $C_3$ to $C_{20}$ olefin further reacted either by grafting a $C_4$ to $C_{20}$ unsaturated nitrogen-containing monomer thereon or by grafting an unsaturated acid onto the polymer backbone and then reacting carboxylic acid groups of the grafted acid with an amine, hydroxy amine or alcohol.

Pour point depressants, otherwise known as lube oil flow improvers (LOFI), lower the minimum temperature at which the fluid will flow or can be poured. Such additives are well known. Typical of those additives that improve the low temperature fluidity of the fluid are $C_8$ to $C_{18}$ dialkyl fumarate/vinyl acetate copolymers, and polymethacrylates. Foam control can be provided by an antifoamant of the polysiloxane type, for example, silicone oil or polydimethyl siloxane.

Some of the above-mentioned additives can provide a multiplicity of effects; thus for example, a single additive may act as a dispersant-oxidation inhibitor. This approach is well known and need not be further elaborated herein.

In the present invention it may also be preferable to include an additive which maintains the stability of the viscosity of the blend. Thus, although polar group-containing additives achieve a suitably low viscosity in the pre-blending stage it has been observed that some compositions increase in viscosity when stored for prolonged periods. Additives which are effective in controlling this viscosity increase include the long chain hydrocarbons functionalized by reaction with mono- or dicarboxylic acids or anhydrides which are used in the preparation of the ashless dispersants as hereinbefore disclosed.

When lubricating compositions contain one or more of the above-mentioned additives, each additive is typically blended into the base oil in an amount that enables the additive to provide its desired function.

When lubricating compositions contain one or more of the above-mentioned additives, each additive is typically blended into the base oil in an amount that enables the additive to provide its desired function. Representative effect amounts of such additives, when used in crankcase lubricants, are listed below. All the values listed are stated as mass percent active ingredient.

TABLE II

| ADDITIVE | MASS % (Broad) | MASS % (Preferred) |
| --- | --- | --- |
| Metal Detergents | 0.1-15 | 0.2-9 |
| Corrosion Inhibitor | 0-5 | 0-1.5 |
| Metal Dihydrocarbyl Dithiophosphate | 0.1-6 | 0.1-4 |
| Antioxidant | 0-5 | 0.01-3 |
| Pour Point Depressant | 0.01-5 | 0.01-1.5 |
| Antifoaming Agent | 0-5 | 0.001-0.15 |
| Supplemental Antiwear Agents | 0-1.0 | 0-0.5 |
| Friction Modifier | 0-5 | 0-1.5 |
| Viscosity Modifier | 0.01-10 | 0.25-3 |
| Basestock | Balance | Balance |

Fully-formulated lubricating oil compositions of the present invention preferably have a TBN of at least 6, such as 6 to 20, preferably at least 8.5, such as from 8.5 to 13, more preferably from 9 to 13 mg, KOH/g (ASTM D4739).

Fully-formulated lubricating oil compositions of the present invention preferably have a sulfated ash (SASH) content (ASTM D-874) of 1.1 or less, preferably 1.0 or less, more preferably 0.8 or less, mass %.

Preferably, fully-formulated lubricating oil compositions of the present invention derive at least 5, such as at least 10, such as at least 15, preferably at least 20, such as at least 25% of the compositional TBN from ashless TBN sources including at least one of the phenylenediamine compounds. More preferably, fully-formulated lubricating oil compositions of the present invention derive at least 5, preferably at least 10, such as at least 15, more preferably at least 20, % of the compositional TBN from at least one of the phenylenediamine compounds, and less than 25, preferably less than 20, more preferably less than 15, % of the compositional TBN from ashless TBN sources other than the phenylenediamine compounds, including basic dispersants.

Fully-formulated lubricating oil compositions of the present invention further preferably have a sulfur content of less than 0.4, more preferably less than 0.35 more preferably less than about 0.03, such as less than 0.15, mass %. Preferably, the Noack volatility (ASTM D5880) of the fully-formulated lubricating oil composition (oil of lubricating viscosity plus all additives and additive diluent) is no greater than 13, such as no greater than 12, preferably no greater than 10. Fully-formulated lubricating oil compositions of the present invention preferably have no greater than 1200, such as no greater than 1000, or no greater than 800, ppm of phosphorus.

It may be desirable, although not essential to prepare one or more additive concentrates comprising additives (concentrates sometimes being referred to as additive packages) whereby several additives can be added simultaneously to the oil to form the lubricating oil composition. A concentrate for the preparation of a lubricating oil composition of the present invention may, for example, contain from 1, such as 1 to 30 mass % of one or more of the phenylenediamine compounds; 10 to 40 mass % of a nitrogen-containing dispersant; 2 to 20 mass % of an aminic antioxidant, a phenolic antioxidant, a molybdenum compound, or a mixture thereof; 5 to 40 mass % of a detergent; and from 2 to 20 mass % of a metal dihydrocarbyl dithiophosphate.

The final composition may employ from 5 to 25, preferably 5 to 18, typically 10 to 15, mass % of the concentrate, the remainder being oil of lubricating viscosity and viscosity modifier.

All weight (and mass) percents expressed herein (unless otherwise indicated) are based on active ingredient (A.I.) content of the additive, and/or additive-package, exclusive of any associated diluent. However, detergents are conventionally formed in diluent oil, which is not removed from the product, and the TBN of a detergent is conventionally provided for the active detergent in the associated diluent oil. Therefore, weight (and mass) percents, when referring to detergents are (unless otherwise indicated) total weight (or mass) percent of active ingredient and associated diluent oil.

This invention will be further understood by reference to the following examples, wherein all parts are parts by weight (or mass), unless otherwise noted.

EXAMPLES

The present invention is illustrated by but in no way limited to the following examples.
TBN Performance The basicity of a lubricating oil composition can be determined by acid titration. The resulting neutralization number is expressed as total base number, or TBN, and can be measured using various methods. Two methods conventionally selected to evaluate ashless base sources are ASTM D4739 (potentiometric hydrochloric acid titration) and ASTM D2896 (potentiometric perchloric acid titration). ASTM D2896 uses a stronger acid than ASTM D4739 and a more polar solvent system. The combination of the stronger acid and more polar solvent results in a more repeatable method that measures the presence of both strong and weak bases. The TBN value as determined by ASTM D2896 is often used in fresh oil specifications. The ASTM D4739 method is favored in engine tests and with used oils to measure TBN depletion/retention. In general, the ASTM D4739 method results in a lower measured TBN value because only stronger basic species are titrated.

Components

The following alkylated phenylenediamines ("PDA's") were used:

PDA1: N,N'-di-(2-ethylhexyl)-p-phenylenediamine
PDA2: N,N'-di-(1,3-dimethylbutyl)-N,N'-di-(2-ethylhexyl)-p-phenylenediamine
PDA3: N,N',N'-tetra-n-heptyl-p-phenylenediamine (comparison)
PDA4: N,N',N'-tetra-n-pentyl-p-phenylenediamine (comparison)
PDA5: N,N'-di-sec-butyl-N,N'-di-n-pentyl-p-phenylenediamine (comparison)

PDA's 1-2 are of the invention; PDA's 3-5 are for comparison. Each PDA was made by using reductive alkylation of the phenylenediamine with an aldehyde or ketone and sodium triacetoxyborohydride in a modification of the method of Abdel-Majid, A. F. et al., 61 J. ORG. CHEM. 3849-62 (1996). Those skilled in the art will recognize that adjustments in stoichiometry, reaction time, and reaction temperature may be required to achieve the desired reaction with varying starting materials. The following examples are illustrative of this method.

Synthesis Examples

PDA 1: N,N'-di-sec-butyl-N,N'-di-(2-ethylhexyl)-p-phenylenediamine

N,N'-di-sec-butyl-p-phenylenediamine (20.8 g, 94 mmol) and sodium triacetoxyhydroborate (60.0 g, 283 mmol) in dichloromethane (500 ml) was treated with 2-ethylhexanal (30.3 g, 236 mmol) and stirred at room temperature for 15 hours. TLC showed the reaction complete and the reaction mixture was decanted to a beaker and quenched by addition of saturated aqueous NaHCO$_3$ and stirred until effervescence ceased. The organic phase was separated and washed twice with water, once with brine and then dried (MgSO$_4$), filtered and concentrated in vaccuo to afford a red oil. The product was chromatographed (eluent 5% ethyl acetate in heptane). Relevant fractions were collected and concentrated to afford a red oil (36.16 g, 82% yield).

PDA2: N,N'-di-(1,3-dimethylbutyl)-N,N'-di-(2-ethylhexyl)-p-phenylenediamine

N,N'-di-(1,3-dimethylbutyl)-p-phenylenediamine (17 g, 61.5 mmol) and 2-ethylhexanal (18.53 g, 144.5 mmol) were dissolved in dichloromethane (500 mL) and were stirred together in a 1 liter round bottomed flask fitted with a condenser and magnetic stirring at room temperature whilst sodium triacetoxyhydroborate (30.63 g, 144.5 mmol) was added portionwise over 1 hour. The mixture was left standing for a total of 18 hours. The crude product was stirred with 150 ml water for a few minutes followed by addition of aqueous sodium carbonate solution (60 g in 250 ml water) in portions. Most of the effervescence subsided after 50% of this had been added. The mixture was stirred with a further 100 ml water and separated using a separating funnel. The organic phase was washed with water (500 ml+750 ml) and brine (500 ml). It was then dried with magnesium sulphate, filtered through celite 521 and evaporated to leave a dark brown oil. The product was chromatographed (eluent 5% EtOAc in heptane). Relevent fractions were combined and concentrated to afford the product as a dark oil (28.6 g, 93% yield).

PDA's 3, 4 and 5 were made by analogous methods.

Lubricants

The amount of basic constituents that are present in the oil can be determined by acid titration. The resulting neutralization number is expressed as the total base number, or TBN. The samples were tested at 1% and 2% treat rates in reference oil in both ASTM methods D2896 and D4739 in order to measure the additional TBN brought by the added PDA. Method D4739 uses a less polar solvent and a weaker acid than D2896 and therefore only the stronger bases are titrated. D4739 is often used as a more accurate measure of the ability of an oil to neutralise acids and the better performance associated with this attribute.

The alkylated phenylenediamine compounds used were the five listed above.

Example 1

A fully-formulated lubricating oil composition containing dispersant, a detergent mixture, antioxidant, ZDDP antiwear agent, pour point depressant and viscosity modifier, in base oil was prepared. The lubricating oil composition, which was representative of a commercial crankcase lubricant, was used as a reference lubricant.

To investigate the performance of the above phenylenediamine compounds 1.00 mass % and 2.00 mass % of PDA1 were respectively added to separate samples of the reference lubricant. An additional amount of base oil was added to each of the samples to provide comparable total mass. The TBN of the resulting samples was determined in accordance with each of ASTM D4739 and ASTM D2896 (in units of mg KOH/g). The results are shown in Table III:

TABLE III

|  | Reference | Sample 1 | Sample 2 |
| --- | --- | --- | --- |
| Reference (g) | 47.50 | 47.50 | 47.50 |
| Added Base Oil (g) | 2.50 | 2.00 | 1.50 |
| PDA1 |  | 0.50 | 1.00 |
| Total Weight (g) | 50 | 50 | 50 |
| TBN by D4739 | 8.67 | 10.07 | 11.54 |
| TBN by D2896 | 9.60 | 12.64 | 14.69 |
| ΔTBN value against reference by D4739 | — | 1.40 | 2.87 |
| ΔTBN value against reference by D2896 | — | 3.04 | 5.09 |

The data of Table III show that PDA1 effectively increased the TBN of the lubricating oil composition as measured by ASTM D2896 and D4739, without contributing to the SASH content.

Examples 2-5

The procedure of Example 1 was repeated using each of PDA's 2-5 in place of PDA 1.

Example 2

PDA2

The results achieved with PDA2 are shown in Table IV:

TABLE IV

|  | Reference | Sample 3 | Sample 4 |
|---|---|---|---|
| Reference (g) | 47.50 | 47.50 | 47.50 |
| Added Base Oil (g) | 2.50 | 2.00 | 1.50 |
| PDA2 |  | 0.50 | 1.00 |
| Total Weight (g) | 50 | 50 | 50 |
| TBN by D4739 | 8.67 | 9.63 | 10.9 |
| TBN by D2896 | 9.60 | 11.29 | 13.63 |
| ΔTBN value against reference by D4739 | — | 0.96 | 2.23 |
| ΔTBN value against reference by D2896 | — | 1.69 | 4.03 |

The data of Table IV show that PDA2 effectively increased the TBN of the lubricating oil composition as measured by ASTM D2896 and ASTM D4739, without contributing to the SASH content.

Example 3

PDA3

The results achieved with PDA3 are shown in Table V:

TABLE V

|  | Reference | Comparative Sample 1 | Comparative Sample 2 |
|---|---|---|---|
| Reference (g) | 95.00 | 95.00 | 95.00 |
| Added Base Oil (g) | 5.00 | 4.00 | 3.00 |
| PDA3 |  | 1.00 | 2.00 |
| Total Weight (g) | 100 | 100 | 100 |
| TBN by D4739 | 8.4 | 9.5 | 10.2 |
| TBN by D2896 | 9.3 | 11.2 | 13.0 |
| ΔTBN value against reference by D4739 | — | 1.1 | 1.8 |
| ΔTBN value against reference by D2896 | — | 1.9 | 3.7 |

The data of Table V show that PDA3 effectively increased the TBN of the lubricating oil composition as measured by ASTM D2896 and ASTM D4739, without contributing to the SASH content.

Example 4

PDA4

The results achieved with PDA4 are shown in Table VI:

TABLE VI

|  | Reference | Comparative Sample 3 | Comparative Sample 4 |
|---|---|---|---|
| Reference (g) | 47.50 | 47.50 | 47.50 |
| Added Base Oil (g) | 2.50 | 2.00 | 1.50 |
| PDA4 |  | 0.50 | 1.00 |
| Total Weight (g) | 50.00 | 50.00 | 50.00 |
| TBN by D4739 | 8.67 | 10.02 | 11.17 |
| TBN by D2896 | 9.51 | 12.56 | 14.74 |
| ΔTBN value against reference by D4739 |  | 1.35 | 2.50 |
| ΔTBN value against reference by D2896 |  | 3.05 | 5.23 |

The data of Table VI show that PDA4 effectively increased the TBN of the lubricating oil composition as measured by ASTM D2896 and ASTM D4739, without contributing to the SASH content.

Example 5

PDA5

The results achieved with PDA5 are shown in Table VII:

TABLE VII

|  | Reference | Comparative Sample 5 | Comparative Sample 6 |
|---|---|---|---|
| Reference (g) | 47.50 | 47.50 | 47.50 |
| Added Base Oil (g) | 2.50 | 2.00 | 1.50 |
| PDA5 |  | 0.50 | 1.00 |
| Total Weight (g) | 50 | 50 | 50 |
| TBN by D4739 | 8.67 | 9.69 | 10.88 |
| TBN by D2896 | 9.60 | 12.48 | 15.39 |
| ΔTBN value against reference by D4739 | — | 1.02 | 2.21 |
| ΔTBN value against reference by D2896 | — | 2.88 | 5.79 |

The data of Table VII show that PDA5 effectively increased the TBN of the lubricating oil composition as measured by ASTM D2896 and ASTM D4739, without contributing to the SASH content.

Example 6

Each of the above type of fully-formulated lubricant was further tested to determine the effect of each of PDA's 1-5 on corrosion and seal compatibility. Corrosion was tested using the high-temperature corrosion bench test (HTCBT) (ASTM D6594), which formulated lubricants must pass before receiving API CJ-4 and ACEA E6 certification. Seal compatibility was evaluated using an industry-standard MB-AK6 test, which must be passed to qualify as a MB p228.51 lubricant. Both seal compatibility and corrosion were tested in the presence of an amount of phenylenediamine compound providing a TBN boost of two (as measured in D4739) over the TBN of the reference oil. The results are shown in Table VIII:

TABLE VIII

| Example | Compound | Calculated TBN Value (mg KOH/g) | Δ TBN by D4739 | Δ TBN by D2896 | HTCBT @ 2TBN (D4739) | MB-AK6 Seals Test @ 2TBN (D4739) |
|---|---|---|---|---|---|---|
| Reference | — | — | — | — | Pass | Pass |
| PDA1 | 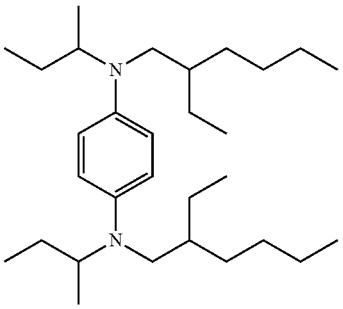 [SMILES: CCCCC(CC)CN(c1ccc(N(CC(CC)CCCC)C(C)CC)cc1)C(C)CC] | 252.3 | 2.0 | 4.0 | Pass | Pass |
| PDA2 | 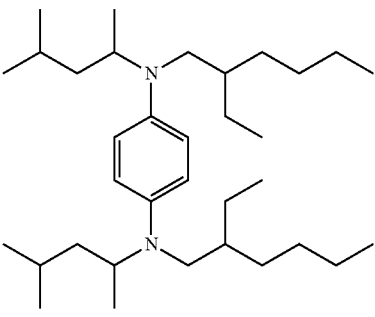 [SMILES: CCCCC(CC)CN(c1ccc(N(CC(CC)CCCC)C(C)CC(C)C)cc1)C(C)CC(C)C] | 223.6 | 2.0 | 4.0 | Pass | Pass |
| PDA3 | 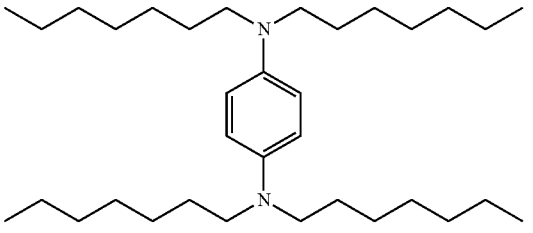 [SMILES: CCCCCCCN(CCCCCCC)c1ccc(N(CCCCCCC)CCCCCCC)cc1] | 223.6 | 1.5 | 3.0 | — | Fail |
| PDA4 | 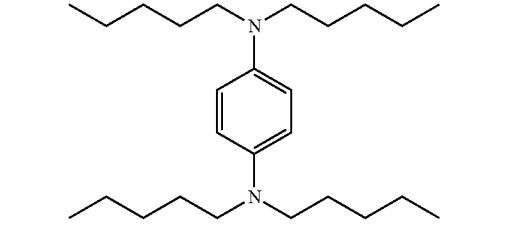 [SMILES: CCCCCN(CCCCC)c1ccc(N(CCCCC)CCCCC)cc1] | 288.4 | 2.0 | 4.0 | Pass | Fail |
| PDA5 | 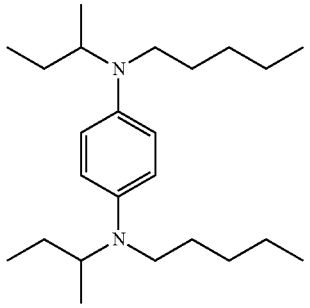 [SMILES: CCCCCN(c1ccc(N(CCCCC)C(C)CC)cc1)C(C)CC] | 310.8 | 2.0 | 4.0 | Fail | Fail |

The data of Table VIII show that PDA1 and PDA2 (of the invention) had no adverse effect on corrosion or seal compatibility when added to the reference oil in an amount providing a TBN boost of two (by D4739). PDAs PDA3 and PDA4 effectively increased the TBN of the lubricating oil composition, as measured by each of D2896 and D4739, but reduced seal compatibility. The addition of PDA5 effectively increased the TBN of the lubricating oil composition, as measured by each of D2896 and D4739 but caused the lubricant to fail the HTCBT test and reduced seal compatibility.

A description of a composition comprising, consisting of, or consisting essentially of multiple specified components, as presented herein and in the appended claims, should be construed to also encompass compositions made by admixing said multiple specified components. The principles, preferred embodiments and modes of operation of the present invention have been described in the foregoing specification. What applicants submit is their invention, however, is not to be construed as limited to the particular embodiments disclosed, since the disclosed embodiments are regarded as illustrative rather than limiting. Changes may be made by those skilled in the art without departing from the spirit of the invention.

What is claimed is:

1. A crankcase lubricating oil composition comprising, or made by admixing, an oil of lubricating viscosity, in a major amount, and, one or more N,N'-tetra-aliphatic hydrocarbyl phenylenediamines, in minor amounts, wherein one or two of said hydrocarbyl groups are branched at an alpha carbon atoms and have 3 to 12 carbon atoms and one or two of said hydrocarbyl groups are branched at a beta carbon atom and have 4 to 12 carbon atoms; any other alkyl group having 1 to 12 carbon atoms.

2. A composition, as claimed in claim 1, wherein said hydrocarbyl groups are alkyl groups.

3. A composition, as claimed in claim 1 having a TBN measured according to ASTM D4739 of at least 6 mg KOH/g.

4. A composition, as claimed in claim 3 having a TBN measured according to ASTM D4739 of from about 6 to about 20 mg KOH/g.

5. A composition, as claimed in claim 1, having a SASH content of no greater than 0.8 mass %.

6. A composition, as claimed in claim 1, wherein at least 10% of the compositional TBN, as measured by ASTM D4739, is derived from said phenylenediamine compounds, and less than 25% of the compositional TBN is derived from ashless TBN sources other than said phenylenediamine compounds.

7. A composition, as claimed in claim 6, wherein at least such as at least 15% of the compositional TBN, as measured by ASTM D4739, is derived from said phenylenediamine compounds.

8. A composition, as claimed in claim 7, wherein at least 25% of the compositional TBN, as measured by ASTM D4739, is derived from said phenylenediamine compounds.

9. A composition, as claimed in claim 6, wherein less than 20% of the compositional TBN is derived from ashless TBN sources other than said phenylenediamine compounds.

10. A composition, as claimed in claim 6, wherein at least 25% of the compositional TBN, as measured by ASTM D4739, is derived from said phenylenediamine compounds, and less than 20% of the compositional TBN is derived from ashless TBN sources other than said phenylenediamine compounds.

11. A composition, as claimed in claim 1, which is a crankcase lubricant for a heavy duty diesel (HDD) engine.

12. A composition, as claimed in claim 1, which has copper corrosion performance in the high-temperature bench corrosion test (ASTM D6594) that falls within the limits of the API CJ-4 and ACEA E6 specification, and has fluoroelastomeric engine seal materials compatibility performance in the MB-AK6 test that falls within the limits of the MB p228.51 specification.

13. A concentrate for the preparation of a lubricating oil composition, as claimed in claim 1, comprising from about 1 to about 30 mass % of one or more of said phenylenediamine compounds; from about 10 to about 40 mass % of a nitrogen-containing dispersant; from about 2 to about 20 mass % of at least one compound selected from an aminic antioxidant, a phenolic antioxidant, and a molybdenum compound; from about 5 to about 40 mass % of a detergent; and from about 2 to 20 mass % of a metal dihydrocarbyl dithiophosphate.

14. A method of lubricating surfaces of a compression-ignited internal combustion engine during its operation comprising:
(a) providing, in a minor amount, one or more N,N'-tetra-aliphatic hydrocarbyl phenylenediamines as defined in claim 1 in a major amount of an oil of lubricating viscosity to make a lubricating oil composition, the TBN of which, as measured by ASTM D4739 is thereby enhanced without concurrently increasing the SASH, and that has copper corrosion performance in the high-temperature bench corrosion test (ASTM D6594) that falls within the limits of the API CJ-4 and ACEA E6 specification, and has fluoroelastomeric engine seal materials compatibility performance in the MB-AK6 test that falls within the limits of the MB p228.51 specification;
(b) providing the lubricating oil composition to the engine crankcase; and
(c) operating said engine.

15. N,N'-tetra-aliphatic hydrocarbyl phenylenediamine of the formula:

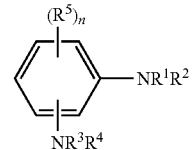

wherein each of $R^1$, $R^2$, $R^3$ and $R^4$ is independently an aliphatic hydrocarbyl group, having 3 to 12 carbon atoms, at least one of $R^1$, $R^2$, $R^3$ and $R^4$ being a hydrocarbyl group branched in the position alpha to the attached nitrogen and having 3 to 12 carbon atoms, and at least one of $R^1$, $R^2$, $R^3$ and $R^4$ being a hydrocarbyl group branched in the position beta to the attached nitrogen, having 4 to 12 carbon atoms; $R^5$, or each $R^5$, is independently hydrogen or an aliphatic hydrocarbyl group, having 1 to 12 carbon atoms; and n is from 0 to 4.

16. Phenylenediamine, as claimed in claim 15, wherein the hydrocarbyl group of one or more of $R^1$, $R^2$, $R^3$ and $R^4$, and $R^5$, when $R^5$ is a hydrocarbyl group, is an alkyl group.

17. Phenylenediamine, as claimed in claim 16, wherein the hydrocarbyl group of each of $R^1$, $R^2$, $R^3$ and $R^4$, and $R^5$, when $R^5$ is a hydrocarbyl group, is an alkyl group.

18. Phenylenediamine, as claimed in claim 15, wherein each of $R^1$ and $R^3$ is independently an alkyl group branched in the position alpha to the attached nitrogen atom, having 3 to 12 carbon atoms; and each of $R^2$ and $R^4$ is independently an alkyl group branched in the position beta to the attached nitrogen atom, having 4 to 12 carbon atoms.

19. Phenylenediamine, as claimed in claim 15, having an average molecular weight of from about 450 to about 700.

20. Phenylenediamine, as claimed in claim 19, having an average molecular weight of from about 450 to about 650.

21. Phenylenediamine, as claimed in claim 20, having an average molecular weight of from about 500 to about 600.

22. Phenylenediamine as claimed in claim 15, wherein the nitrogen atoms are arranged para to one another.

23. N,N'-di-(s-butyl)-N,N'-di-(2-ethylhexyl)-p-phenylenediamine.

24. N,N'-di(1,3-methylbutyl)-N,N'-di(2-ethylhexyl)-p-phenylenediamine.

25. Phenylenediamine, as claimed in claim 15, having a TBN, measured as in ASTM D4739, of at least 50 mg KOH/g.

26. Phenylenediamine, as claimed in claim 25, having a TBN, measured as in ASTM D4739, of at least 120 mg KOH/g.

27. A mixture of phenylenediamine compounds as claimed in claim 15.

* * * * *